(12) United States Patent
Gho

(10) Patent No.: US 8,870,905 B2
(45) Date of Patent: Oct. 28, 2014

(54) METHOD FOR IN VIVO MULTIPLICATION OF HAIR

(75) Inventor: Conradus Ghosal Gho, Bunde (NL)

(73) Assignee: Hair Science Institute, Amsterdam (NL)

( * ) Notice: Subject to any disclaimer, the term of this patent is extended or adjusted under 35 U.S.C. 154(b) by 1801 days.

(21) Appl. No.: 12/094,688

(22) PCT Filed: Nov. 22, 2006

(86) PCT No.: PCT/NL2006/000588
§ 371 (c)(1), (2), (4) Date: Apr. 30, 2009

(87) PCT Pub. No.: WO2007/061291
PCT Pub. Date: May 31, 2007

(65) Prior Publication Data
US 2010/0034856 A1    Feb. 11, 2010

(30) Foreign Application Priority Data

Nov. 22, 2005   (NL) ..................................... 1030484

(51) Int. Cl.
*A61K 35/36* (2006.01)
*A61Q 7/00* (2006.01)
*A61K 8/98* (2006.01)
*A61K 35/12* (2006.01)

(52) U.S. Cl.
CPC . *A61K 35/36* (2013.01); *A61Q 7/00* (2013.01); *A61K 35/12* (2013.01); *A61K 8/985* (2013.01)
USPC .......................... 606/187; 424/93.7; 424/70.1

(58) Field of Classification Search
None
See application file for complete search history.

(56) References Cited

U.S. PATENT DOCUMENTS

| 6,399,057 B1 | 6/2002 | Gho |
| 2004/0054410 A1 | 3/2004 | Barrows |
| 2005/0089512 A1 | 4/2005 | Schlotmann et al. |

FOREIGN PATENT DOCUMENTS

| EP | 0236014 A1 | 9/1987 |
| EP | 0971679 A1 | 1/2000 |

*Primary Examiner* — Michael G Hartley
*Assistant Examiner* — Nabila Ebrahim
(74) *Attorney, Agent, or Firm* — John S. Sopko; Hoffmann & Baron, LLP

(57) ABSTRACT

A method is described for the reproduction of hair by removing hair in the anagen phase in such a way that the hair stem cells which are responsible for hair growth are still attached to the hair removed, bringing these into contact with extracellular matrix components or substitutes therefor, and implanting the hair in the scalp. The application of extracellular matrix components or substitutes therefor for the reproduction of hair is also described.

3 Claims, No Drawings

METHOD FOR IN VIVO MULTIPLICATION OF HAIR

CROSS-REFERENCE TO RELATED APPLICATIONS:

This application is the National Stage of International Application No. PCT/NL2006/000588, filed Nov. 22, 2006, which claims the benefit of Netherlands Application No. NL 1030484, filed Nov. 22 2005, the contents of which is incorporated by reference herein.

FIELD OF THE INVENTION:

This invention relates to a method for the reproduction of hair.

BACKGROUND OF THE INVENTION:

The essential growth structures of hair are the so-called hair follicles which are present in the skin. These hair follicles produce hair follicle cells or keratinocytes. During their journey to the surface of the skin the cytoplasm of these cells is converted by a large number of complex processes into the tough and elastic material which is known as hair. The growth cycle of hair can be subdivided into three phases: the anagen phase ('growth phase'), the catagen phase ('transitional phase') and the telogen phase ('death phase'). The hair follicle is unique in the cyclic nature of hair formation and hair growth. It is the only part of the body that has a growth nucleus, from which new hairs can be produced after removal of the old hair.

Human beings usually find baldness undesirable from a cosmetic and aesthetic point of view. Baldness occurs frequently, however, and it is a known phenomenon that men in particular become balder as they get older. It does also occur in women, however, and is then in particular highly undesirable from a cosmetic and aesthetic point of view.

A known technique for combating baldness is the transplantation of hair. With this procedure hair, including the skin, is removed from a donor area covered with hair which is often located on the back of the head, and is cut into small pieces which usually only contain one to three hairs. These pieces are then implanted in the bald area (receptor area). A significant disadvantage of this technique is that this is at the expense of the donor area. After all, hair is removed from this area and this hair does not grow back. This transplantation technique therefore offers limited possibilities.

It is known that hair follicle cells can be cultured from plucked human hair. It is also known that it is difficult to form a differentiated epidermis or a completely developed epidermis with the aid of such cultured cells, both in vitro and in vivo. Cultured hair follicle cells from mice can stimulate hair growth when they are implanted in test animals.

A method for the reproduction of hair in human beings is described in European patent application 0 236 014, in which epidermal follicle cells of the desired hair type are removed from the head hair of a patient. The epidermal follicle cells are then cultured in a culture medium which preferably contains growth factors. An opening is then made in the epidermis of the patient's scalp and the cultured epidermal follicle cells are introduced via this opening into the dermis next to the epidermis. The disadvantage of this method is that it includes an invasive method and that the cells are not placed in a targeted manner, so that many cells are needed and the probability of the regeneration of hair is less.

Another method for the reproduction of hair is described in European patent application 0 971 679. Here the hair is removed from a donor area in such a way that new hairs come back in place thereof, while new hair follicle cells are cultured from the hairs removed, from which cells can once again form new hair. Renewed hair growth can thus be achieved without this being at the expense of the donor area. To this end hair follicle cells removed in the anagen phase are cultured for 1 hour to 40 days in a serum-free keratinocyte culture medium. A disadvantage of this method is the long time that is needed for culturing the hair follicle cells.

SUMMARY OF THE INVENTION:

It is the object of this invention to overcome one or more of the above-mentioned problems, and thus to provide a method for the reproduction of human hair in which a long culturing time is not required. Extracellular matrix is produced by the (support) cells around the hair follicle. From our own research it is apparent that this Extracellular Matrix is essential for hair growth. In this invention the hairs are no longer cultured in a keratinocyte culture medium but are simply immersed for a short time in a medium which contains extracellular matrix or substitutes therefor. The hair is then put back. With this technique several hairs can grow as a result of putting back a single hair. The method according to the invention is moreover patient-friendly, because only plucked hairs can be used and no invasive method or anaesthesia is necessary, the patient does not have to come back for a second treatment after culturing in order to have the hairs implanted after culturing. A further advantage is that the donor area is left intact.

DETAILED DESCRIPTION OF PREFERRED EMBODIMENTS:

This invention thus relates to a method for the reproduction of hair, which method comprises the following steps:
 (a) removing hair in the anagen phase from one or more donor areas in such a way that the hair stem cells which are responsible for hair growth are still attached to the hair removed; and
 (b) bringing the hair removed into contact with a medium which contains extracellular matrix components or substitutes therefor; and
 (c) implanting the hair of step b) in the scalp.

According to this invention it is thus not necessary to culture the hair follicle cells; merely immersing the hair in the medium which contains extracellular matrix components or substitutes therefor is sufficient. The hair is then put back in the scalp, after which several hairs grow out of this one hair.

In step a) of the method according to this invention hair in the anagen phase is removed from one or more donor areas in such a way that the hair stem cells which are responsible for hair growth are still attached to the hair removed.

As has already been stated above, hair growth comprises three phases: an anagen, catagen and telogen phase. Only hairs which are in the anagen phase are suitable for the method according to the invention. Compared with hairs in the catagen and telogen phase such hairs in the anagen phase are characterized in that they have a bulbus—often pigmented—with a shape that is characteristic of hairs in the anagen phase, on the underside of the hair. This is generally known and a hair in the anagen phase is therefore immediately recognizable for an experienced eye by the shape of the bulbus. Use of a microscope can give a definitive answer in cases of doubt. The removal of hair in the anagen phase can be effected in various ways, provided that the bulbus which is characteristic of hair in the anagen phase is still attached to the hair removed.

Since the difference between hairs in the different growth phases is very clearly visible when the hairs have been removed, the hairs are for example removed from the donor area by plucking hair from the donor area and selecting the hairs plucked in the anagen phase. Tweezers are for example highly suitable for plucking hair from the donor area. The hair can also be plucked from the scalp by hand, however.

In step b) of the method according to the invention the hair removed is brought into contact with a medium which contains extracellular matrix components or substitutes therefor.

To this end a plucked hair can for example be immersed for a short time, e.g. 2 seconds, in the medium which contains extracellular matrix components or substitutes therefor. A longer contact time between the hair removed and the medium which contains extracellular matrix components or substitutes therefor is of course also possible but is not required. The culturing step which is described in European patent application 0 971 679 is thus not needed.

The term "extracellular matrix components" is a term known to all in the art. Substitutes therefor are also known in the art. Examples of Extracellular Matrix components are collagen, laminin, etc. These components are already available for cell culture. Examples thereof are Collagen I to IV inclusive, from Sigma/Aldrich, or Alminin, from Merck.

It is not necessary for the whole hair to be immersed in the medium which contains extracellular matrix components or substitutes therefor. Immersing the part of the hair to which the stem cells are attached is sufficient for the reproduction of hair by the method according to this invention.

In the last step c) the hair of step b) is implanted in the scalp. This hair—or at least the part of the hair to which the stem cells are attached—has been in contact with a medium which contains extracellular matrix components or substitutes therefor, and probably as a consequence of this the hair stem cells which are located in that part have been 'activated', so that they too can develop into hairs. As a consequence of this the implantation of the single hair of step b) results in the growth of one or several hairs.

The medium which contains extracellular matrix components or substitutes therefor preferably has a viscous consistency (e.g. a hydrogel). As used here, the term "medium" refers to a substance which contains important nutritional components, such as growth factors and trace elements.

As has already been discussed above, it is preferable that hair in the anagen phase is removed by plucking the hair from one or more donor areas, followed by selection of suitable hairs in the anagen phase.

The invention furthermore relates to the application of extracellular matrix components or substitutes therefor for the reproduction of hair. Such an application of extracellular matrix components has not been described previously.

What is claimed is:

1. A method for the reproduction of hair, which method comprises the following steps:
    (a) removing hair in the anagen phase from one or more donor areas in such a way that the hair stem cells which are responsible for hair growth are still attached to the hair removed; and
    (b) contacting the hair stem cells of the hair removed in step (a) with a medium which contains extracellular matrix components for a short time-period of about 2 seconds; and
    (c) implanting the hair of step (b) in the scalp.

2. The method according to claim 1, in which the medium which contains extracellular matrix components has a viscous consistency.

3. The method according to claim 1, in which hair in the anagen phase is removed by plucking the hair from one or more donor areas, followed by selection of suitable hairs in the anagen phase.

* * * * *